United States Patent
Beckman et al.

(10) Patent No.: US 8,348,917 B2
(45) Date of Patent: Jan. 8, 2013

(54) STRETCHED, NECKED, UNITARY GARMENT AND A METHOD OF MANUFACTURING SAME

(75) Inventors: LuAnn M Beckman, Neenah, WI (US); Paul T VanGompel, Hortonville, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 480 days.

(21) Appl. No.: 11/950,999

(22) Filed: Dec. 5, 2007
(Under 37 CFR 1.47)

(65) Prior Publication Data
US 2009/0149828 A1  Jun. 11, 2009

(51) Int. Cl.
*A61F 13/15* (2006.01)
*A61F 13/20* (2006.01)

(52) U.S. Cl. ........ 604/385.101; 604/385.01; 604/385.22

(58) Field of Classification Search .................. 604/367, 604/385.01, 385.22, 385.101
See application file for complete search history.

(56) References Cited

U.S. PATENT DOCUMENTS

| | | |
|---|---|---|
| 3,424,162 A | 1/1969 | Parravicini |
| 4,205,679 A | 6/1980 | Repke et al. |
| 4,610,681 A | 9/1986 | Strohbeen et al. |
| 4,641,381 A | 2/1987 | Heran et al. |
| 4,646,362 A | 3/1987 | Heran et al. |
| 4,690,681 A | 9/1987 | Haunschild et al. |
| 4,720,415 A | 1/1988 | Vander Wielen et al. |
| 4,756,709 A | 7/1988 | Stevens |
| 4,847,134 A | 7/1989 | Fahrenkrug et al. |
| 5,026,364 A | 6/1991 | Robertson |
| 5,114,781 A | 5/1992 | Morman |
| 5,116,662 A | 5/1992 | Morman |
| 5,352,216 A | 10/1994 | Shiono et al. |
| 5,376,198 A | 12/1994 | Fahrenkrug et al. |
| 5,439,459 A | 8/1995 | Tanji et al. |
| 5,846,232 A | 12/1998 | Serbiak et al. |
| 6,159,191 A | 12/2000 | Mishima et al. |
| 6,262,331 B1 | 7/2001 | Nakahata et al. |
| 6,375,646 B1 | 4/2002 | Widlund et al. |
| 6,468,630 B1 | 10/2002 | Mishima et al. |
| 6,482,191 B1 | 11/2002 | Roe et al. |

(Continued)

FOREIGN PATENT DOCUMENTS

EP  1201212  2/2002

(Continued)

OTHER PUBLICATIONS

Abstract of JP 03224559 published Oct. 3, 1991.

(Continued)

*Primary Examiner* — Michele M Kidwell
(74) *Attorney, Agent, or Firm* — Dority & Manning, P.A.

(57) ABSTRACT

An absorbent article can utilize a chassis design comprising a unitary inner layer and an expandable absorbent assembly attached to the inner layer, with the inner layer including elasticized portions so that the absorbent article conforms to the body of a person wearing the article. The expandable absorbent assembly can be minimally attached to the garment side of the inner layer and, in some embodiments at an aperture or opening in the inner layer that allows exudates to pass into the absorbent assembly. The article can further comprise an extensible outer layer attached to the garment side of the inner layer so that the outer layer covers the absorbent assembly and elastics, with the outer layer attached at the perimeter of at least portions of the article.

7 Claims, 4 Drawing Sheets

U.S. PATENT DOCUMENTS

| | | |
|---|---|---|
| 6,502,250 B2 | 1/2003 | Suga et al. |
| 6,570,056 B1 | 5/2003 | Tanzer et al. |
| 6,579,274 B1 | 6/2003 | Morman et al. |
| 6,605,070 B2 | 8/2003 | Ludwig et al. |
| 6,620,146 B2 | 9/2003 | Gibbs |
| 6,627,564 B1 | 9/2003 | Morman et al. |
| 6,632,212 B1 | 10/2003 | Morman et al. |
| 6,842,191 B1 | 1/2005 | Smith |
| 6,964,720 B2 | 11/2005 | Schneider et al. |
| 7,150,730 B2 | 12/2006 | Hasler et al. |
| 7,220,335 B2 | 5/2007 | Van Gompel et al. |
| 2002/0169432 A1 | 11/2002 | Fell et al. |
| 2003/0125696 A1 | 7/2003 | Morman et al. |
| 2004/0002689 A1 | 1/2004 | Igaue et al. |
| 2004/0186452 A1 | 9/2004 | Sandin et al. |
| 2005/0143710 A1* | 6/2005 | Van Gompel et al. ........ 604/393 |
| 2006/0089615 A1 | 4/2006 | Saito |
| 2007/0048497 A1 | 3/2007 | Zhou et al. |
| 2007/0049895 A1* | 3/2007 | Van Gompel et al. . 604/385.101 |
| 2007/0117481 A1 | 5/2007 | Day et al. |

FOREIGN PATENT DOCUMENTS

| | | |
|---|---|---|
| EP | 1578326 | 9/2005 |
| EP | 1578330 | 9/2005 |
| EP | 1578333 | 9/2005 |
| JP | 03224559 | 10/1991 |
| JP | 03251245 | 11/1991 |
| JP | 11276523 | 10/1999 |
| JP | 2001258931 | 9/2001 |
| JP | 2001293030 | 10/2001 |
| JP | 05120516 | 5/2005 |
| KR | 10 00217211 | 9/1999 |
| KR | 10 2003 0094411 | 12/2003 |
| KR | 10 2006 0109966 | 10/2006 |
| KR | 10 0587860 | 11/2006 |
| WO | WO 9616624 | 6/1996 |
| WO | WO 9739711 | 10/1997 |
| WO | WO 9743994 | 11/1997 |
| WO | WO 9900095 | 1/1999 |
| WO | WO 0047152 | 8/2000 |
| WO | WO 0143968 | 6/2001 |
| WO | WO 02085273 | 10/2002 |
| WO | WO 03037213 | 5/2003 |
| WO | WO 03043530 | 5/2003 |
| WO | WO 2004012640 | 2/2004 |
| WO | WO 2005065609 | 7/2005 |
| WO | WO 2006093443 | 9/2006 |

OTHER PUBLICATIONS

Abstract of JP 03251245 published Nov. 8, 1991.
Abstract of JP 11276523 published Oct. 12, 1999.
Abstract of JP2001258931 published Sep. 25, 2001.
Abstract of JP2001293030 published Oct. 23, 2001.
Abstract of JP 2005120516 published May 12, 2005.
International Search Report, PCT/IB2008/053752, Dated Sep. 16, 2008.

* cited by examiner

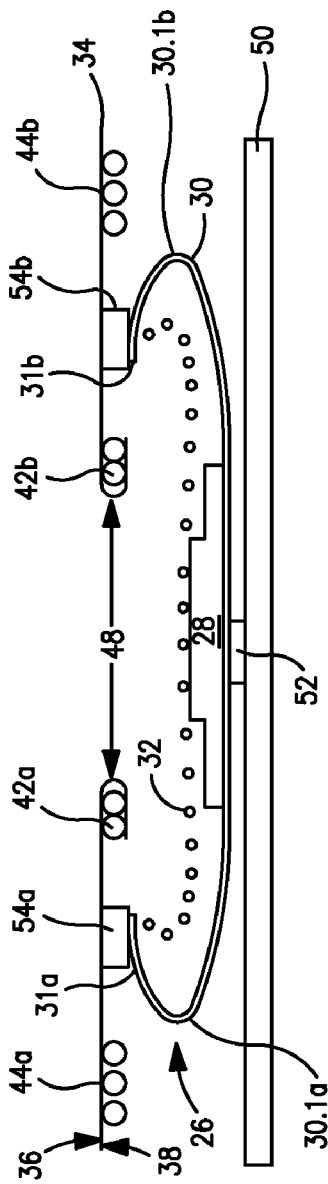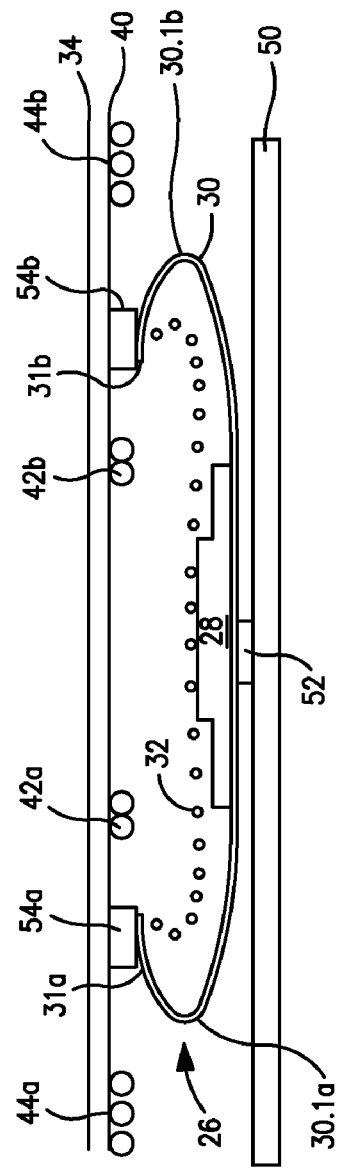
FIG. 1A
FIG. 1B

STRETCHED, NECKED, UNITARY GARMENT AND A METHOD OF MANUFACTURING SAME

BACKGROUND

Individuals wear absorbent articles to receive and contain discharged urine, perspiration, fecal matter, and/or other body exudates. For instance, absorbent articles can include, but are not limited to, diapers, training pants, and other garments, such as adult incontinence products and feminine hygiene products. Some conventional designs for absorbent articles comprise a fluid impervious top sheet that faces the wearer of the article, an absorbent core or material, and a fluid impervious back sheet. In some such designs, elasticized material, such as LYCRA strands can be sandwiched between the edges of the back sheet and top sheet and thereby create an (ideally) fluid-impervious leg and/or waist gasket. However, such an architecture for an absorbent garment is not ideal in all situations.

SUMMARY

As set forth in detail below, in accordance with one or more aspects of the present subject matter, an absorbent article can utilize a chassis design comprising a unitary inner layer and an expandable absorbent assembly attached to the inner layer, with the inner layer including elasticized portions so that the absorbent article conforms to the body of a person wearing the article. The expandable absorbent assembly can be minimally attached to the garment side of the inner layer and, in some embodiments at an aperture or opening in the inner layer that allows exudates to pass into the absorbent assembly. The article can further comprise an extensible outer layer attached to the garment side of the inner layer so that the outer layer covers the absorbent assembly and elastics, with the outer layer attached at the perimeter of at least portions of the article.

A chassis design can overcome problems that may be encountered in the use of absorbent articles comprising a top sheet facing the wearer, a back sheet, and absorbent core positioned between the top sheet and back sheet. For instance, red marks and other irritations from the leg elastics can be reduced or avoided through use of a chassis design featuring a unitary inner layer. Additionally or alternatively, leakage gaps at the legs and/or waist due to stiffness in the top sheet/absorbent core/back sheet composite can be avoided. Additionally, the absorbent article may have the look and feel of underwear due to the unitary nature of the layer facing the wearer as well as the manner in which the outer layer is attached to the remaining components of the article.

BRIEF DESCRIPTION OF THE DRAWINGS

A full and enabling disclosure of the present invention, including the best mode thereof to one of ordinary skill in the art, is set forth more particularly in the remainder of the specification, including reference to the accompanying figures in which.

Figure 1:
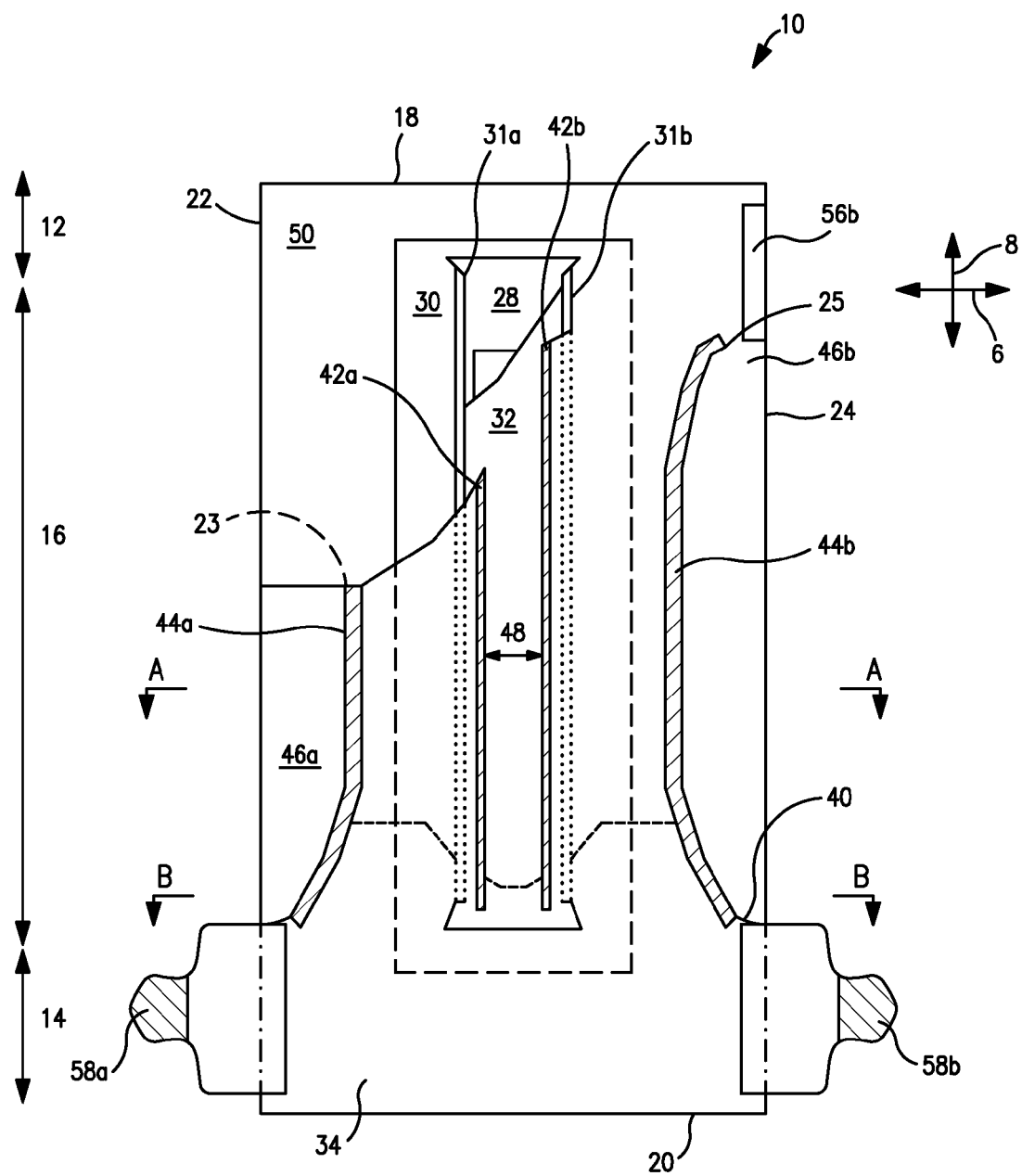
FIG. 1 is a cutaway diagram showing an exemplary article constructed in accordance with aspects of the present subject matter, with FIGS. 1A and 1B depicting cross-sectional views of the exemplary article shown in FIG. 1.

Repeat use of reference characters in the present specification and drawings is intended to represent same or analogous features or elements of the present disclosure.

DETAILED DESCRIPTION

An absorbent article can define a longitudinal axis and a lateral axis perpendicular to the longitudinal axis and feature a front waist region, a back waist region and a crotch region positioned between the front waist region and the back waist region along the longitudinal axis. Two sides can define the outer boundaries of the garment along the lateral axis. The crotch and waist regions are intended as generalized descriptions of regions of the article and do not represent a precise location on the article. For example, the relative size, length, and other characteristics of the front and back waist regions and crotch region can vary according to the article design, intended use, article size, and other details of its construction.

In any event, the article can comprise an absorbent assembly and a unitary inner layer, with the unitary inner layer comprising a body side that faces a wearer of the article when worn, and a garment side opposite the body side and facing the absorbent assembly. The inner layer can be extensible at the waist regions at least in the lateral direction and may be further extensible in the longitudinal direction at the crotch region. The article can comprise at least one waist panel attached to the garment side of the inner layer at each of the front and back waist regions, with each of the waist panels comprising a material that is elastic in at least the lateral direction, with the material unstretched when the article is in a substantially laid-flat state.

The term "laid-flat state" is intended to refer to the article when it is flattened into a plane or is substantially flattened into a plane and is used in contrast to when the article otherwise positioned, such as when the article is folded or shaped in or for use by a wearer.

The article can further comprise at least one flap elastic attached to the garment side of the inner layer on each side of the crotch region, with each flap elastic comprising elastic material that is stretched in the longitudinal direction when the article is in a substantially laid-flat state. The at least one flap elastic may be further stretchable or may be at or approaching its maximum stretch value when the article is in a laid-flat state.

The article can further comprise at least one leg elastic attached to the garment side of the inner layer in a stretched state and on each side of the article, with each leg elastic defining a leg opening when the article is worn. Generally speaking, the leg elastics will partially or fully encircle the area at which a user's leg is intended to exit the article when the article is worn. The leg elastics may generally extend in the longitudinal direction, although ends of the leg elastic on each side may curve outward toward the side in some embodiments.

In some embodiments, the inner layer can comprise an aperture at the crotch region extending in the longitudinal direction with the flap elastics positioned along the longitudinal edges of the aperture. For example, the aperture may comprise a slit in the inner layer along the longitudinal axis or may comprise a larger opening along the longitudinal axis that also extends towards each side of the article in the lateral direction. In such embodiments, the aperture may comprise any suitable shape, such as a generally oval-shaped, rectangular, or other suitable opening in the inner layer. In some embodiments, the aperture may extend partially into the portions of the front and/or back waist regions adjacent to the crotch region.

In some embodiments, the absorbent assembly can comprise a liner, a core, and a fluid impervious back sheet. For instance, the absorbent assembly may be attached to the garment side of the inner layer between the flap elastics and the leg elastics so that the aperture at the crotch region opens into the absorbent assembly.

In some embodiments, the absorbent assembly can comprise a "c-folded" assembly which, when viewed cross-sectionally along the longitudinal axis of the article, comprises a fold on each side of the assembly that defines the outer most lateral points of the assembly, with at least part of the assembly extending from the fold back towards the center of the garment (i.e. away from each respective side of the garment) and towards the garment side of the inner layer, with the side edges of the assembly attached to the garment side of the inner layer.

In some embodiments, the article can comprise an extensible outer cover attached along the perimeter of the crotch region and at the center of the absorbent assembly. The extensible outer cover may additionally or alternatively be attached to the perimeter of the article at the waist panels. In some embodiments, the inner layer can extend longitudinally and laterally beyond the edges of the absorbent assembly. Thus, in some embodiments, the absorbent assembly may have room to expand when body exudates, such as urine, fecal matter and/or other material, is deposited therein by the wearer of the article.

A method of manufacturing a stretched, necked, unitary garment can comprise unwinding an extensible inner layer in a machine direction. The inner layer can comprise two side edges extending in the machine direction that define the side edges of the inner layer. The method can further comprise attaching a plurality of elastic panels that are stretchable in the cross machine direction (i.e. perpendicular to the machine direction) to the extensible inner layer, with one panel defining a front waist region of a garment being manufactured and the other panel defining a back waist region of the garment being manufactured. The panels can be spaced apart from one another in the machine direction to define a crotch region comprising the area between the front and back waist regions.

In some embodiments, the method can comprise attaching panels spaced apart in the machine direction. A portion of each panel can comprise the front waist region of a first garment, with the remaining portion of each panel comprising the back waist region of a second garment adjacent along the machine axis. Once manufacturing is complete, each garment can be separated by cutting in the cross-machine direction across the panels.

The method can further comprise attaching a plurality of stretched flap elastics to the inner layer at the crotch region and extending in the machine direction, with the flap elastics spaced apart from one another in the cross machine direction to define an aperture region. The method can further comprise attaching at least one stretched leg elastic to the inner layer on each side of the crotch region between the flap elastic and inner layer side edge to define a plurality of elasticized leg regions. For instance, the leg elastic or elastics on each side can define the boundary of areas which will later be removed in order for a wearer's legs to pass through a completed garment when worn.

The method can further comprise attaching an absorbent assembly to the inner layer at the edges of the aperture region. The absorbent assembly may itself comprise multiple components that are attached or otherwise brought together prior to being attached to the garment being manufactured. For example, an exemplary absorbent assembly may comprise a liner, an absorbent core, and backsheet. The components of the absorbent assembly may be attached to one another or otherwise arranged as a unit in any suitable way.

The method can further comprise placing an extensible outer layer over the garment being manufactured and attaching the outer layer to the edges of the article at the waist panels and the elasticized leg regions. For example, the outer layer can be attached at the perimeter of the waist panels and along the elasticized leg regions to cover elasticized regions and the absorbent assembly.

The method can further comprise cutting out leg regions at each side of the garment along or near the elasticized leg regions and attaching front and back fasteners to the garment. The particular type and arrangement of fasteners can vary according to the particular garment being manufactured. For example, tab fasteners may be attached in suitable locations so that the absorbent article can be placed on an infant or other diaper user. As another example, fasteners may be included along the side edges at the waist regions so that the waist regions can be brought together and permanently or removably attached to form a training undergarment or adult incontinence product. Alternatively, the front and back waist regions may be removably or permanently joined together to form a pre-assembled training pant, incontinence product, or other undergarment.

In some embodiments, attaching an absorbent assembly can comprise attaching the edges of a "c-folded" assembly to the inner layer between the flap elastics and the elasticized leg regions. The edges of the assembly may extend out from the center of the assembly toward the sides of the garment and then back toward the center of the garment and toward the inner layer.

In some embodiments, the absorbent assembly can also be attached to the front and back waist panels in addition the inner layer. For example, the absorbent assembly may extend beyond the crotch region and into the front and/or back waist regions where the assembly is attached to the waist panels. In some embodiments, the length of the absorbent assembly, however, may be less than the length of the garment in the machine direction regardless of whether the absorbent assembly extends beyond the crotch region. Furthermore, as measured in the cross-direction, the width of the absorbent assembly may be less than the width of the inner layer and may be less than the width of the garment.

FIG. 1 is a cutaway diagram showing an exemplary article 10 constructed in accordance with aspects of the present subject matter. Generally, for purposes of this discussion, reference will be made to a longitudinal axis indicated at 8 and a lateral axis indicated at 6 with the lateral and longitudinal axes perpendicular to one another. Absorbent article 10 defines a front waist region 12, a back waist region 14, and a crotch region 16 located between the front and back waist regions.

Absorbent article 10 uses a unitary chassis design, separate panels or other components are not used to form discrete waist and crotch regions. Thus, the particular locations of the waist regions and crotch region are for purposes of example and explanation only, and the relative sizes of such region and the boundaries therebetween will vary according to the particular dimensions and use scenarios for an absorbent article.

Absorbent article 10 extends from a front waist edge 18 along the longitudinal axis to a back waist edge 20 and from a first side edge 22 over to a second side edge 24 in the lateral direction. Unless specifically noted otherwise, reference to the "sides" of the article refers to the lateral edges. Some embodiments of absorbent articles may be formed by using a rectangular-shaped inner layer and then cutting out leg regions. Thus, leg section final side edges 23 and 25 are illustrated in FIG. 1 to represent the ultimate lateral boundaries of absorbent article 10. In addition to FIG. 1, the following examples will be best understood with reference to FIG. 1A, which is a cross-sectional view of absorbent article 10 taken along the lines A-A in FIG. 1 and FIG. 1B, which is a view taken along lines B-B in FIG. 1 showing the cross-section of article 10 at the back waist region.

Absorbent article 10 comprises an absorbent assembly 26 which, in this example, comprises an absorbent core 28, a fluid-impervious back sheet 30, and a top sheet or liner 32. As best seen in FIGS. 1A and 1B, absorbent assembly 26 in this example forms a three layer structure wherein absorbent core 28 is sandwiched between liner 32 and back sheet 30. Back sheet 30, liner 32, and absorbent core 28 are also visible in the cutaway view of FIG. 1.

Absorbent article 10 comprises inner layer 34, which includes a body side 36 which faces the user of the article when worn and a garment side 38 which is opposite body side 36. Inner layer 34 extends the length of absorbent article 10 and extends the width of absorbent article 10 as well. Absorbent article 10 further comprises front waist elastic panel 39 (not shown in FIG. 1) and back waist panel 40. The front and back waist panels can comprise any suitable material that is elastic in at least the lateral direction. For example, either or both waist panels may comprise an elastic single-faced neck bonded laminate such as is described in U.S. Patent Application Pre-Grant Publication No. 20070048497, which is incorporated by reference in its entirety herein. Front and back waist panels 39 and 40 are attached to garment side 38 of inner layer 34 to impart lateral elasticity to inner layer 34. The front and back waist panels can be attached to layer 34 in any suitable way, including by adhesive, ultrasonic bonding, heat bonding, and/or any other suitable technique or techniques. In some embodiments, the front and back waist panels are attached so that the panels are in an unstretched state when the article is in a laid-flat or substantially laid-flat condition. Thus, the front regions of the article can be stretched in the lateral direction when the article is worn.

Absorbent article 10 further comprises flap elastics 42A and 42B which extend along the longitudinal axis from the front waist region 12 through the crotch region 16 to the back waist region 14. For example, in some embodiments, each flap elastic 42 comprises one or a plurality of elastic strands. Flap elastics 42A and 42B are attached at the garment side 38 of inner layer 34 with an aperture region therebetween. In some embodiments, flap elastics 42 are attached to inner layer 34 so that, when absorbent article 10 is in a laid-flat or a substantially laid-flat state, elastics 42 are partially or fully stretched. Flap elastics 42 may comprise any suitable material, such as a Findley hot melt elastic, such as is described in U.S. Pat. No. 4,704,116. In some embodiments, the flap elastics 42 comprise elastic material sold under the trade name LYCRA SPANDEX.

Absorbent article 10 can further comprise leg elastics 44A and 44B which also generally extend in the longitudinal direction of the article. Like flap elastics 42, leg elastics 44 can each comprise one or more strands of elastic material, although other embodiments need not necessarily use strands. Although FIGS. 1A and 1B illustrate strands with a circular cross-section, other types and/or numbers of strands may be used. Depending upon the configuration of the article, leg elastics 44 may curve outward at either or both the front and back waist regions. Generally speaking, leg elastics 44 will define the outer edge of the garment at the leg areas when it is worn and form cuffs encircling the legs of the wearer of the article. As was noted above, leg section final side edges 23 and 25 are shown in FIG. 1 as coextensive with respective leg elastics 44a and 44B. Thus, although absorbent article 10 is shown as having a generally rectangular shape, at or before the time of use, leg cut out regions 46A and 46B may be removed from the article (e.g. as a phase of manufacturing the article). Although in these examples leg elastics 44 are coextensive with the leg cuffs, in other embodiments, additional cuff material may be included at the leg openings for aesthetic and/or functional purposes and/or leg elastics 44 may be slightly offset from side edges 23 and 25.

As was noted above, in some embodiments, absorbent article 10 can comprise an aperture region which can be cut, slit, or otherwise opened to form an aperture 48 in inner layer 34. Aperture 48 extends along the longitudinal axis in crotch region 16 of absorbent article 10, and ends at or near the interface between crotch region 16 and waist region 12/waist region 14. In some embodiments, aperture 48 may comprise a slit in inner layer 34, while in other embodiments, the aperture may comprise a more substantial opening. For example, an absorbent article may include an oval-shaped opening extending along the longitudinal axis but also extending outward towards the sides of the article along the lateral axis. Other aperture shapes, such as squares, rectangular, or irregular shapes, may also be utilized. Generally speaking, aperture 48 allows urine, fecal matter, and/or other body exudates to pass into and be absorbed by absorbent structure 26. The material from inner layer 34 at aperture 48 may be removed to form aperture 48. In some embodiments, however, material corresponding to aperture 48 remains attached as flaps at or near aperture 48.

In operation, absorbent structure 26 absorbs exudates from the wearer of the article. For example, liner 32 may comprise any suitable material, such as material used as the inner liner in composite absorbent articles that do not use a chassis structure of the present subject matter. For example, liner 32 may be a liquid-permeable material that allows exudates to pass through layer 32 to be absorbed by absorbent core 28. Back sheet 30, on the other hand, may comprise a liquid-impervious material so that material that passes into absorbent structure 26 does not pass out of absorbent structure 26. Furthermore, in some embodiments, liner 32 may allow exudates to pass in from aperture 48 but may be configured so that exudates do not pass in the other direction (i.e. a one-way material).

In some embodiments, the absorbent structure 26 may comprise what is referred to herein as a "c-folded" assembly. As best seen in FIGS. 1A and 1B, the assembly comprises a fold that extends along each lateral side of the assembly, with the fold defining the outermost lateral point of the assembly on each side, with the folds shown at 30.1A and 30.1B. The assembly then extends from each fold back towards the center of the article (i.e. away from the respective side of the garment) and towards the garment side 38 of inner layer 34 to form the "C" shape visible in FIGS. 1A and 1B. Of course, the fold does not necessarily need to form a perfect "C" shape, nor do the folds on each side of the assembly need to be symmetrical. Liner 32 also forms a similar shape, although the particular points on liner 32 are not illustrated for purposes of clarity. In the examples of FIG. 1, the side edges 31A and 31B of the absorbent structure 26 are attached to the garment side 38 of inner layer 34 at respective attachment points 54A and 54B.

Assembly 26 is attached at points which lie between leg elastics 44 and flap elastics 42. For example, 54A and 54B may comprise strips, beads, or other portions of adhesive or other material used to join the ends of the absorbent assembly to the inner layer 34. As another example, 54A and 54B may represent bonding or weld points. Regardless of the attachment mechanism or mechanisms used, flap elastics 42 can position aperture 48 for optimal reception of exudates without interference from absorbent structure 26. Absorbent structure 26 is positioned to expand in some embodiments to accommodate body exudates without interfering with or requiring attachment to structures such as leg elastics 44. Since leg elastics 44 are not required for containment purposes, different elastic materials and/or different elastic strengths can be selected that result in a more comfortable fit for wearers of the article.

Absorbent article 10 may further comprise outer cover 50 which is positioned to face garment side 38 of inner layer 34 such that outer cover 50 covers elastics 44 and absorbent structure 26. As shown in FIGS. 1A and 1B, outer cover 50 is attached at 52 to the center of absorbent structure 26 so that this minimal attachment can further allow for the expansion of absorbent structure 26 as needed. Outer cover 50 may further be attached to the waist and crotch regions of the garment along the perimeter of absorbent article 10. For example, outer cover 50 may be attached along waist edges 18 and 20, along leg elastics 44, and along the portions of side edges 22 and 24 that are between the waist edges and leg elastics on the front and back waist regions.

FIG. 1 further illustrates attachment tabs 58A and 58B configured to interface with and attach to the garment side of the outer layer. Any suitable fastening mechanism or mechanisms may be used, including adhesives, hook-and-loop fastener systems, and/or other fastening means.

This example further illustrates a secondary fastener 56B (with a corresponding secondary fastener 56A not shown in this figure due to the cutaway view). The secondary fasteners may have a high coefficient of friction or engage into the back waist region body side of the inner layer when the garment is applied to a wearer. The secondary fasteners can keep the front ears of the diaper from shifting during wear.

Although these examples depict an absorbent article 10 in the form of a diaper, other absorbent articles may comprise training pants, disposable undergarments, or other pant-like products that may be joined, for example through bonding or welding the front and back waist regions together in a permanent or detachable manner.

Figure 2:
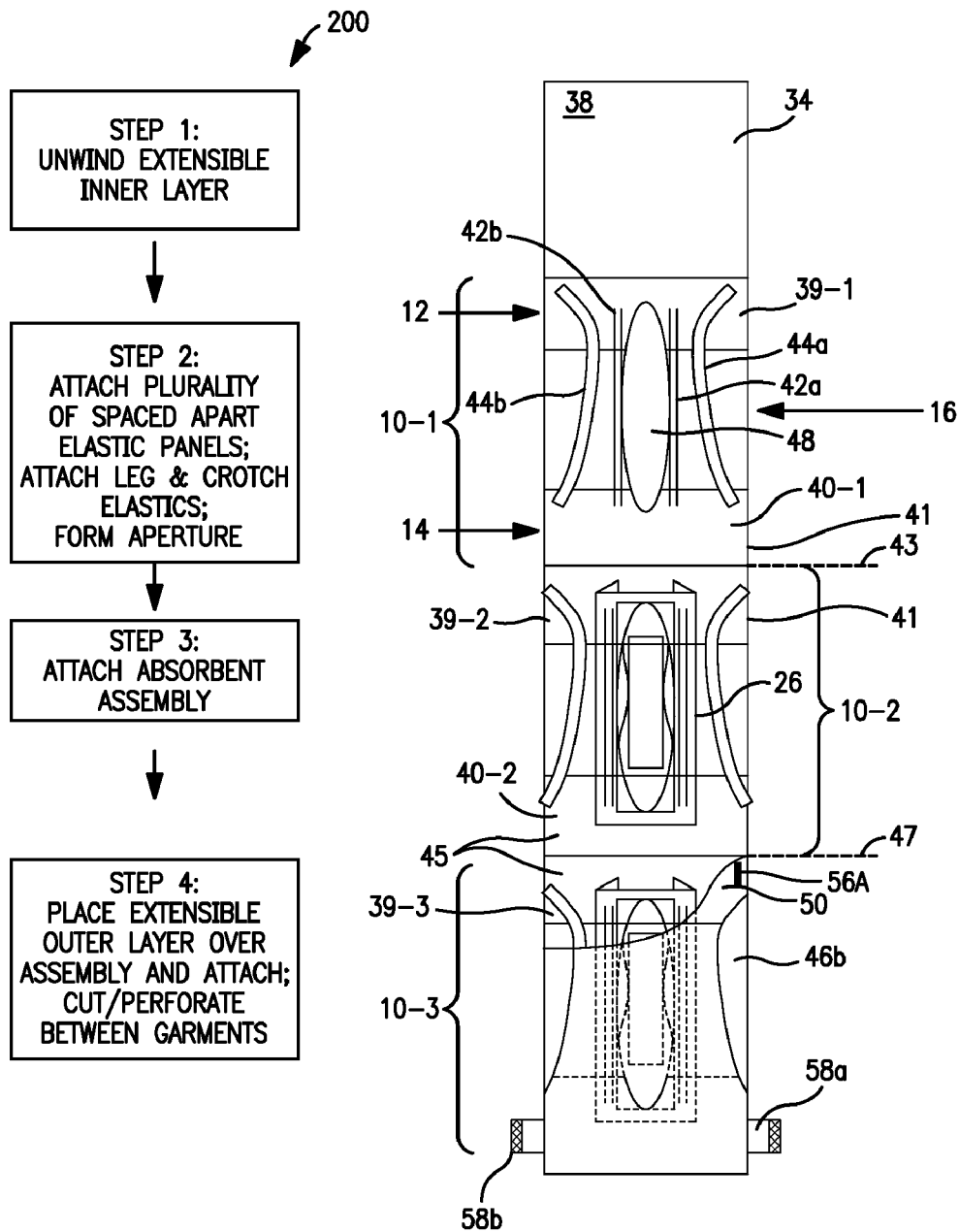
FIG. 2, shows an exemplary series of steps for constructing a stretched, necked unitary garment.

Turning now to FIG. 2, an exemplary series of steps for constructing a stretched, necked unitary garment will now be discussed in conjunction with flowchart 200. Exemplary manufacturing operations will be discussed with reference to a series of phases of construction of the article as represented by three exemplary articles 10-1, 10-2, and 10-3. Articles 10-1, 10-2, and 10-3 are depicted alongside the exemplary steps of the method to show the state of completion after each respective step.

Construction/configuration of the actual equipment and apparatus used to carry out the exemplary manufacturing operations should be within the skill of one of ordinary skill in the art after review of this disclosure; therefore, the details of operating particular components that could be used in manufacturing, such as material unwinding/unrolling, adhesive application, bonding equipment, and the like are not discussed in detail. Furthermore, the division of tasks into the steps of this example are not meant to be limiting; in other embodiments, aspects of the different steps could be combined or separated into distinct sub-steps as appropriate.

Initially, at step 1, the extensible inner layer material 34 is unwound to serve as a base for the other materials/components of the articles. Namely, the inner layer material 34 is unwound in a machine direction indicated as MD in FIG. 2. In this example, the garment side 38 is visible. At step 2, front waist elastic panel 39 and back waist elastic panel 40 are attached at respective portions of inner layer material in a spaced-apart manner to define a region therebetween comprising crotch region 16. The elastic panels 39 and 40 define front waist region 12 and back waist region 14 of each garment (illustrated as 39-1, 40-1, 39-2, 40-2, and so on to indicate panels of respective garments). In some embodiments, panels 39 and 40 are attached in a relaxed (i.e. non-stretched) state. As was noted above, the location of the boundary between the crotch region and front/back waist regions can vary according to the configuration of the article and intended use(s) of the article. For instance, the "crotch" region may actually comprise portions of the article that comprise elastic waist panel 39 and/or waist panel 40.

In some embodiments, step 2 comprises placing elastic panels which will ultimately be split into multiple garments. For instance, rather than placing an individual front waist panel 39 and back waist panel 40 for each garment, composite panels may be placed, with a portion of each panel comprising a front waist region of a first garment and the other portion of each panel comprising a back waist region of a second garment adjacent to the first garment along the axis of the machine direction. For example, in FIG. 2, panels 40-1 and 39-2 may be placed as a single panel 41 which is later cut or perforated along separation line 43 to define the back waist panel 40-1 of garment 10-1 and the front waist panel 39-2 of garment 10-2. Similarly, panels 40-2 and 39-3 may initially comprise a single panel 45 which is cut or perforated along separation line 47 to separate garments 10-2 and 10-3.

Although this example shows the separation line between garments adjacent along the axis of the machine direction to be perpendicular to the axis, it will be understood that, in other embodiments, the line followed by the cuts or perforations between garments may occur at any suitable angle, and can comprise any suitable shape. Separation between garments can occur once the composite has been fully assembled, either as part of the manufacturing process or by the end user as will be noted below.

After waist panels have been attached, flap elastics 42a and 42b are attached to the article spaced apart in the cross-machine direction, with leg elastics 44a and 44b also attached to the article in a spaced-apart manner. As indicated in FIG. 2, each leg elastic 44 lies between a respective side edge of inner layer 34 and a flap elastic 42. Flap elastics 42 and leg elastics 44 may be applied in any sequence or simultaneously. Flap elastics 42 and 44 are partially or wholly stretched in the machine direction at the time of attachment in some embodiments.

An aperture 48 can be formed in the aperture region between flap elastics 42. For instance, inner layer 34 may be cut or slit to create an opening of any suitable size or shape in the area between flap elastics 42. Garment 10-1 represents an article under manufacture after completion of step 2.

At step 3, an absorbent assembly 26 is attached to each garment being manufactured. Garment 10-2 represents an absorbent article after completion of step 3. For instance, absorbent assembly may comprise a C-folded assembly. In such embodiments, the inward-folded edges can be attached to the outboard edges of the aperture 48. For instance, the edges of the C-folded assembly may be attached at the flap elastics 42 or between the flap elastic 42 and leg elastic 44 on each side. Absorbent assembly 26 may also be attached to front waist panel 39 and back waist panel 40 on the garment side of each such panel.

At step 4, an extensible outer layer 50 can be placed over the entire assembly and perimeter attached to the article. For example, in some embodiments, the assembly can be attached at the front and back waist edges, along the side edges of the front and back waist regions, and along the final side edges of the leg openings. After outer layer 50 is attached, leg regions can be cut using dies or otherwise removed to create the curved elastic leg openings. Furthermore, fasteners such as 56b and 58b can be attached to the garment side of outer layer 50 at appropriate locations to facilitate wearing of each garment. Depending on packaging and marketing concerns, garments may be separated into individual units and/or the separation line between garments (e.g. the line defining the border between back waist region 14 of a first article and front waist region 12 of a second article along the machine axis) may be perforated to facilitate later separation by a user.

Figure 3:
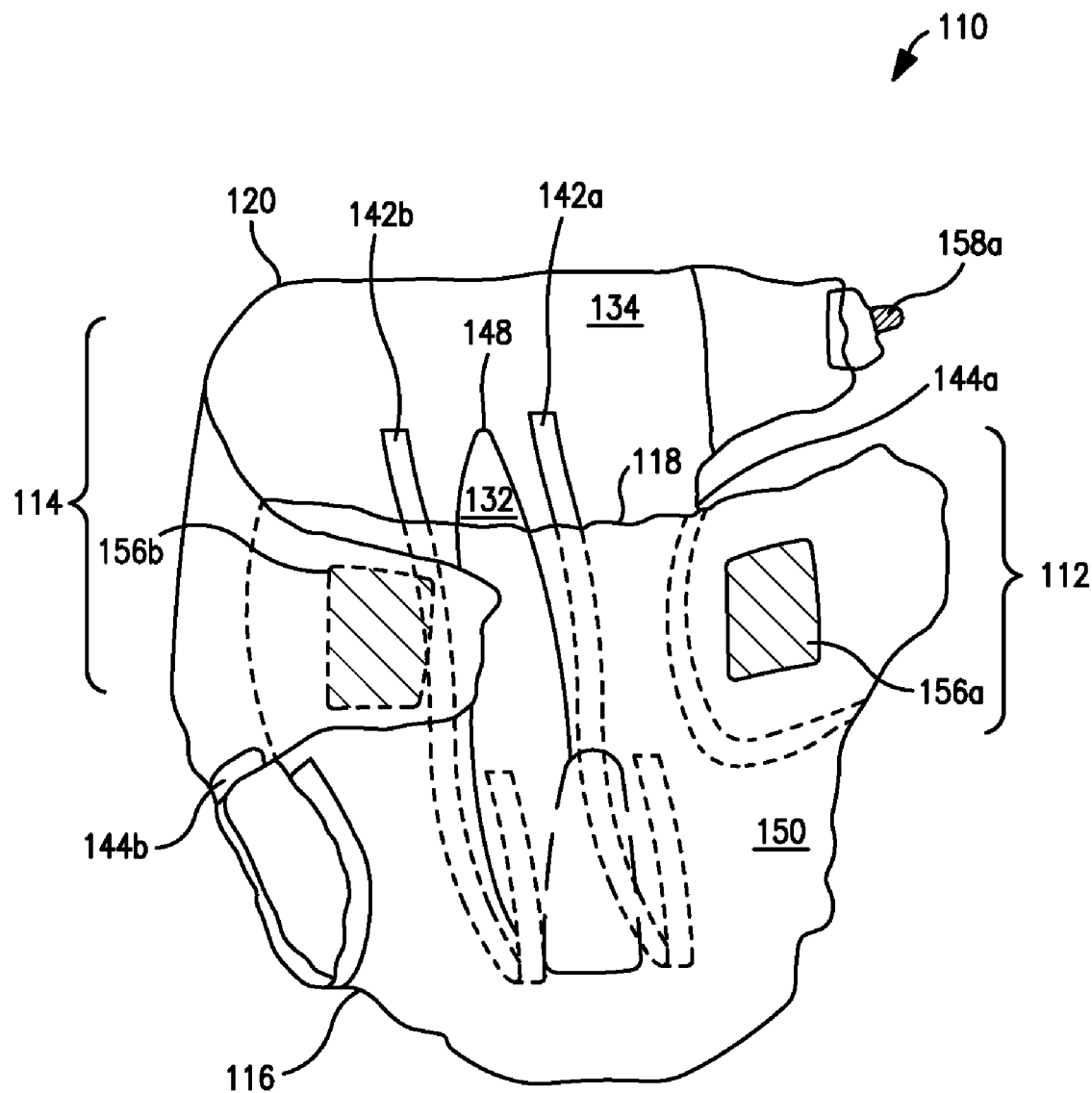
FIG. 3 is a perspective view depicting the exterior of an exemplary absorbent article in a completed state showing how the article is positioned to be worn by a user.

Briefly, FIG. 3 is a perspective view depicting the exterior of another exemplary absorbent article 110 in a completed state to show how the article is positioned to be worn by a user. Namely, fastening mechanism 158B has been brought into contact with front waist region 112 at one side of the article such that one ear of the diaper wraps around as it would when article 110 is worn. Secondary fastener 156B is in contact with the body side of the inner layer of the ear portion. Outer layer 150 is visible at the exterior of the article facing the viewer. Body side 136 of inner layer 134 is visible inside the article. The other side of the article is shown with fasting mechanism 158A disengaged and corresponding portions of waist areas 112 and 114 separated from one another.

Flap elastics 142b and 142a are in a spaced-apart arrangement with aperture 148 therebetween. Liner 132 of an absorbent assembly (the remainder of which is not illustrated in FIG. 3) is visible through aperture 148. Although not shown in FIG. 3, the sides of aperture 148 may be retained to serve as flaps that partially or wholly cover aperture 148 but allow exudates to pass therethrough (by passing through the flap material and/or between the flaps, for instance).

Leg elastic 144b is shown forming a leg cuff through which a wearer's leg may pass when the article is worn. Leg elastic 144a is shown as partially forming a cuff that can be completed by fastening together the corresponding front and back waist regions of the article. When worn, flap elastics can serve to position aperture 148 to receive exudates from the wearer of the article. The absorbent assembly, which can be attached at the perimeter of aperture 148 or between flap elastics 142 and leg elastics 144, serves to contain the exudates without the need for leg elastics 144 to maintain a watertight fit. Thus, article 110 may be more comfortable to the wearer while also presenting the look and feel of underwear due to the unitary nature and appearance of inner layer 134 and outer layer 150.

Although not discussed in detail in the examples above, any suitable materials suitable for use in an absorbent product can be used in implementing embodiments of the present subject matter. For instance, any of inner layer 34 (134), outer layer 50 (150), absorbent assembly liner 32, absorbent assembly back sheet 30, and/or other components of the article can comprise suitable woven, nonwoven, or composite materials. Materials such as the absorbent assembly back sheet 30 may be innately impervious to moisture or may be rendered impervious through use of additives, coatings, and/or addition of other layers or films of material. Elastic portions, such as flap elastics 42 (142), leg elastics 44 (144), front waist panel 39, and back waist panel 40, can be implemented using any material with suitable elastic properties.

These and other modifications and variations to the present invention may be practiced by those of ordinary skill in the art, without departing from the spirit and scope of the present invention, which is more particularly set forth in the appended claims. In addition, it should be understood that aspects of the various embodiments may be interchanged both in whole or in part. Furthermore, those of ordinary skill in the art will appreciate that the foregoing description is by way of example only, and is not intended to limit the invention so further described in such appended claims.

What is claimed:

1. An absorbent article defining a longitudinal axis and a lateral axis perpendicular to the longitudinal axis, the article defining a front waist region, a back waist region, a crotch region between the front waist region and the back waist region, and two sides defining the outer boundaries of the garment along the lateral axis, the article comprising:
   an absorbent assembly;
   a unitary inner layer comprising a body side that faces a wearer of the article and a garment side opposite the body side and facing the absorbent assembly, wherein the unitary inner layer is free of separate panels, the inner layer being extensible at the waist regions in the lateral direction and;
   at least one waist panel attached to garment side of the inner layer at each of the front and back waist regions, each at least one waist panel comprising material that is elastic in at least the lateral direction;
   at least one flap elastic attached to the garment side of the inner layer on each side of the crotch region and comprising elastic material stretched in the longitudinal direction when the article is in a substantially laid-flat state;
   wherein the inner layer comprises an aperture at the crotch region extending in the longitudinal direction and the at least one flap elastic is positioned along at least one longitudinal edge of the aperture such that the at least one flap elastic is the closest elastic to the aperture;
   at least one leg elastic attached to the garment side of the inner layer in a stretched state and on each side of the article, each leg elastic defining a leg opening when the article is worn; and
   where the absorbent assembly comprises a liner, core, and fluid-impervious backsheet wherein the absorbent assembly is attached to the garment side of the inner layer between the at least one flap elastic and the at least one leg elastic so that the aperture at the crotch region opens into the absorbent assembly.

2. The article set forth in claim 1, wherein the inner layer is extensible in the longitudinal direction at the crotch region.

3. The article set forth in claim 1, wherein at least one waist panel comprises material that is unstretched when the article is in a substantially laid-flat state.

4. The article as set forth in claim 1,
   wherein the absorbent assembly comprises a C-folded assembly which, when viewed cross-sectionally along the longitudinal axis of the article, comprises a fold along each side of the assembly defining the outermost lateral points of the assembly, with the assembly extending from the fold at each side away from the sides of the garment and towards the garment side of the inner layer; and
   wherein the side edges of the assembly are attached to the garment side of the inner layer.

5. The article as set forth in claim 1, wherein each waist region defines a perimeter and the article comprises an extensible outer cover attached to each waist panel along the perimeter.

6. The article set forth in claim 1, wherein the article comprises an extensible outer cover attached along the perimeter of the crotch region and at the center of the absorbent assembly.

7. The article as set forth in claim 1, wherein the inner layer extends longitudinally and laterally beyond the edges of the absorbent assembly.

* * * * *